United States Patent [19]
Lekholm

[11] Patent Number: 4,694,830
[45] Date of Patent: Sep. 22, 1987

[54] HEART PACEMAKER WITH RESPIRATORY SIGNAL GENERATION CAPABILITY

[75] Inventor: Anders Lekholm, Bromma, Sweden

[73] Assignee: Siemens Aktiengesellschaft, Berlin and Munich

[21] Appl. No.: 911,057

[22] Filed: Sep. 24, 1986

[30] Foreign Application Priority Data

Oct. 4, 1985 [DE] Fed. Rep. of Germany ....... 3535534

[51] Int. Cl.[4] .......................... A61N 1/00; H05G 0/00
[52] U.S. Cl. ........... 128/419 PG; 128/419 D:419 PT; 128/421
[58] Field of Search ............ 128/419 D, 419 PT, 421, 128/422

[56] References Cited

U.S. PATENT DOCUMENTS

| | | | |
|---|---|---|---|
| 3,523,539 | 8/1970 | Lavezzo ................................ | 128/422 |
| 3,593,718 | 7/1971 | Krasner .............................. | 128/419 P |
| 4,567,892 | 2/1986 | Plicchi et al. ................. | 128/419 PG |
| 4,574,810 | 3/1986 | Lerman ........................... | 128/419 D |
| 4,596,251 | 6/1986 | Plicchi et al. ................. | 128/419 PG |

FOREIGN PATENT DOCUMENTS

| | | | |
|---|---|---|---|
| 0009255 | 4/1980 | European Pat. Off. ........ | 128/419 D |
| 0089014 | 9/1983 | European Pat. Off. ..... | 128/419 PG |
| 2070282 | 9/1981 | United Kingdom ......... | 128/419 PG |

OTHER PUBLICATIONS

Siemens brochure, "Der diagnostische multiprogrammierbare physiologische impulsgenerator 674".

Primary Examiner—William E. Kamm
Assistant Examiner—Timothy J. Keegan
Attorney, Agent, or Firm—Hill, Van Santen, Steadman & Simpson

[57] ABSTRACT

A heart pacemaker has circuitry for forming an electrical signal corresponding to the electrode impedance of the pacemaker. The signal is formed by monitoring the stimulation current and the stimulation voltage and dividing those values by each other in a divider. This impedance signal is a measure of the respiration rate of the pacemaker user, and is employed for controlling the pulse rate of the pulse generator of the heart pacemaker in accordance therewith.

3 Claims, 4 Drawing Figures

HEART PACEMAKER WITH RESPIRATORY SIGNAL GENERATION CAPABILITY

BACKGROUND OF THE INVENTION

The present invention relates to heart pacemakers, and in particular to a heart pacemaker having the capability of controlling the output pulse rate of the pacemaker in accordance with changing respiration characteristics of the pacemaker user.

During respiration of a patient, the electrical impedance between two electrodes on the chest of the patient changes. By monitoring this impedance, it is thus possible to calculate the respiration rate and deepness of breathing of the patient. The ventilated breath volume per minute can in turn be calculated therefrom.

It is an object of the present invention to provide a heart pacemaker having the capability of forming electrical signals which are dependent upon the respiration of the pacemaker user, and employing the respiration signals for physiological control of the pacemaker output.

The above object is achieved in accordance with the principles of the present invention by a pacemaker having circuitry for forming electrical signals corresponding to the stimulation current and to the stimulation voltage. The pacemaker includes a divider for these signals which forms an impedance signal corresponding to the electrode impedance. The impedance signal is supplied to a control stage for the pacemaker pulse generator after a signal component dependent upon the respiration has been filtered therefrom. The portions of the impedance signal dependent upon the respiration of the patient can then be employed for theraputically controlling the pulse generator of the pacemaker. In contrast to conventional respiration methods, the respiration signal in the pacemaker described herein is acquired from the stimulation pulses by the standard stimulation electrode, without the use of additional measuring electrodes and the accompanying additional measuring energy which is necessary in known devices.

At rest, normal respiration rates are between 10 and 20 respiratory cycles per minute. Because the normal heart pacemaker stimulation rate is about 70 stimulation pulses per minute, roughly 5 measuring events for the electrode impedance can be executed per respiration cycle. This is entirely adequate for acquiring the respiration rate and the volume of breath per minute.

In a heart pacemaker wherein the stimulation rate is variable, the relationship of the heart stimulation rate and respiration can be maintained given intensification of respiration (increase in the respiratory rate). It is also possible to employ a varying sampling rate for measuring the respiration parameters.

DESCRIPTION OF THE PREFERRED EMBODIMENTS

Figure 1:
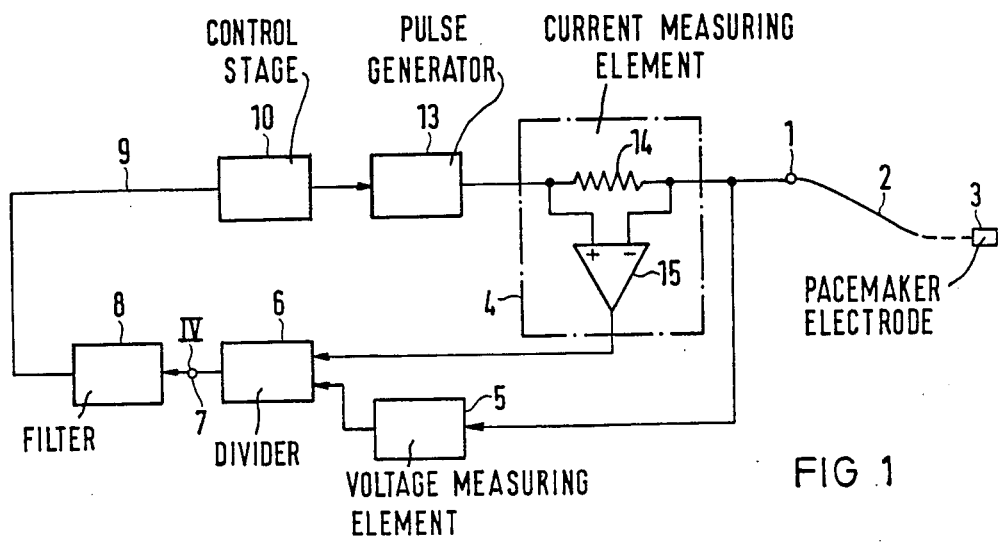
FIG. 1 is a schematic block diagram of a heart pacemaker having respiratory signals generation capability constructed in accordance with the principles of the present invention.

A heart pacemaker constructed in accordance with the principles of the present invention is shown in a first embodiment in FIG. 1. The pacemaker includes a terminal 1 to which a lead 2 is connected which terminates in a pacemaker electrode 3. The pacemaker includes a pulse generator 13. Stimulation pulses supplied by the pulse generator 13 flow through a resistor 14. The resistor 14 and an amplifier 15 form a current measuring element 4. The voltage of the stimulation pulses is measured by a voltage measuring element 5. A divider 6 is supplied with the outputs of the current measuring element 4 and the voltage measuring element 5 and the divider 6 forms an electrical signal from those inputs by division. This electrical signal at the output 7 of the divider 6 corresponds to the electrode impedance. A filter 8 filters the signal components from the output of the divider which are dependent upon the respiration. The output of the filter 8, which corresponds to the respiratory rate of the pacemaker user, is supplied via line 9 to a control stage 10, which controls operation of the pulse generator 13 dependent upon the respiratory rate, such as by varying the pacemaker output pulse rate.

A filter 8 filters the signal components from the output of the divider which is dependent upon respiration. The two main components of the impedance signal are the stroke volume variations and the variations due to respiration. The stroke volume variations have a frequency of about 103 Hz corresponding to normal heart rates between 60 and 180 beats per minute. The respiratory signal has a lower frequency range, normally between 10 and 30 breaths per minute, i.e. 0.16 to 0.5 Hz.

A standard low-pass filter with an appropriate cut-off frequency and design to dampen the stroke volume signals and other signals above 1 Hz will adequately filter out the respiratory component of the signal.

Figure 2:
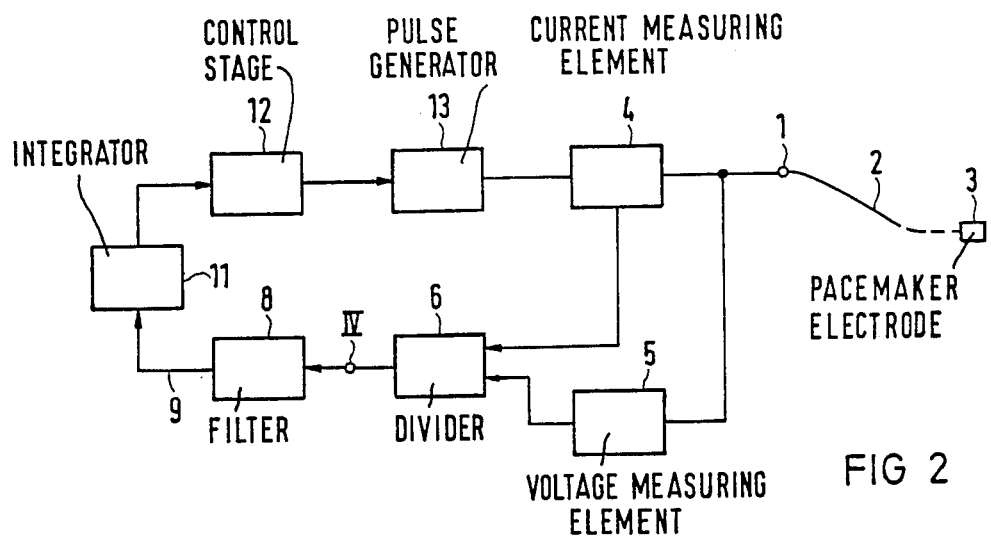
FIG. 2 is a schematic block diagram of a further embodiment of the pacemaker shown in FIG. 1.

Another embodiment of a pacemaker constructed in accordance with the principles of the present invention is shown in FIG. 2, wherein elements corresponding to the elements already described in connection with FIG. 1 are provided with identical reference symbols. In the embodiment of FIG. 2, the signal on line 9 corresponding to the respiratory rate is supplied to an integrator 11 which forms a signal corresponding to the respiration volume per minute therefrom. The output of the integrator 11 is supplied to a control stage 12 for controlling the pulse generator 13 dependent upon the respiratory volume, such as by varying the output pulse rate.

In each of the embodiments of FIGS. 1 and 2, respiration of the patient is monitored via the electrode impedance of the heart pacemaker, and a respiratory rate signal or a respiratory volume per minute signal is formed. These signals are then used to control the pulse rate of the pulse generator 13 of the heart pacemaker.

Figure 3:
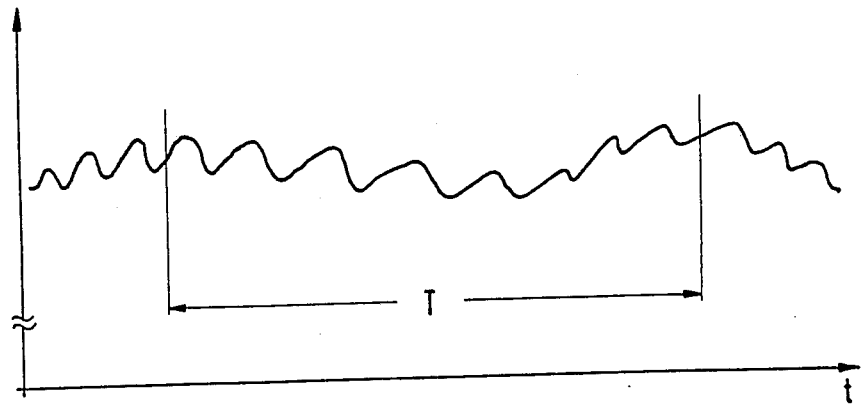
FIG. 3 is a graph showing the variation of the electrode impedance with respect to time.

A chronological curve of the electrode impedance is shown in FIG. 3. A respiratory interval T is also shown in FIG. 3. It can be seen that the electrode impedance fluctuates cyclically with the respiration.

Figure 4:
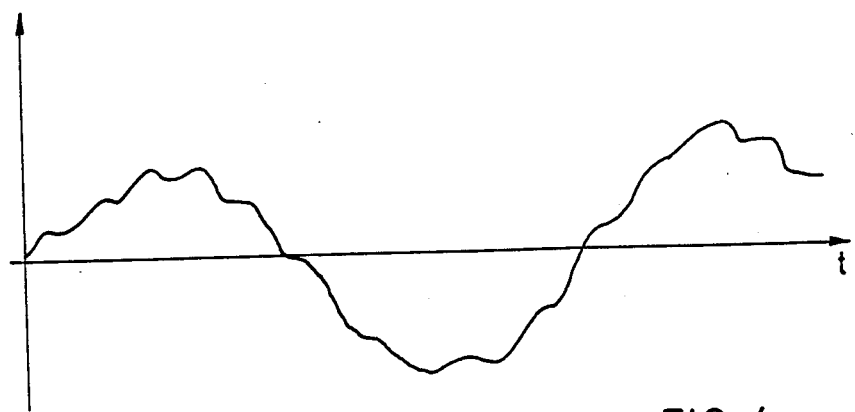
FIG. 4 is a graph showing the voltage occurring at node IV in FIG. 1.

The voltage at node IV in FIGS. 1 and 2 is shown in FIG. 4. This is the signal which is generated dependent upon the respiration of the patient acquired by measurement of the electrode impedance.

Although modifications and changes may be suggested by those skilled in the art it is the intention of the inventor to embody within the patent warranted hereon all changes and modifications as reasonably and properly come within the scope of his contribution to the art.

I claim as my invention:

1. In a heart pacemaker for supplying stimulation pulses to a heart via a pacemaker electrode, the improvement comprising:

means connected to said pacemaker electrode for measuring the stimulation current;

means connected to said pacemaker electrode for measuring the stimulation voltage;

a divider connected to said means for measuring the stimulation current and means for measuring the stimulation voltage for forming an impedance signal corresponding to the electrode impedance;

means for generating a signal corresponding to the respiration rate of said pacemaker user from said impedance signal and for controlling the pulse rate of said pacemaker dependent thereon.

2. A pacemaker as claimed in claim 1, wherein said means for generating a signal corresponding to said respiration rate of said pacemaker user includes a filter connected to the output of said divider for filtering a respiration-dependent portion of said impedance signal out of said impedance signal.

3. A pacemaker as claimed in claim 1, further comprising an integrator to which said signal corresponding to the respiration of said pacemaker user is supplied for generating a signal corresponding to the respiration volume in a selected period of said pacemaker user.

* * * * *